United States Patent [19]

De Bernardo et al.

[11] 3,998,999
[45] Dec. 21, 1976

[54] PROCESS FOR PREPARING PYRAZOMYCIN AND PYRAZOMYCIN B

[75] Inventors: Silvano De Bernardo, Montclair; Manfred Weigele, North Caldwell, both of N.J.

[73] Assignee: Hoffmann-La Roche Inc., Nutley, N.J.

[22] Filed: Oct. 20, 1975

[21] Appl. No.: 624,074

[52] U.S. Cl. .................................. 536/1; 424/180
[51] Int. Cl.² .......................................... C07H 3/02
[58] Field of Search .............. 260/209 R, 211.5 R; 536/1

[56] References Cited
UNITED STATES PATENTS 3,674,774  7/1972  Williams et al. ............. 260/209 R
3,755,293  8/1973  Shirato et al. ................ 260/209 R Primary Examiner—Johnnie R. Brown
Attorney, Agent, or Firm—Samuel L. Welt; Bernard S. Leon; Frank P. Hoffman

[57] ABSTRACT

This invention is directed to a synthetic process to produce the pharmacologically active compounds
3-(1'-α-D-ribofuranosyl)-4-hydroxyrazole-5-carboxamide (Pyrazomycin B) and
3-(1'-β-,D-ribofuranosyl)-4-hydroxypyrazole-5-carboxamide (Pyrazomycin)

The pyrazomycins exhibit activity as antiviral and antitumor agents.

4 Claims, No Drawings

PROCESS FOR PREPARING PYRAZOMYCIN AND PYRAZOMYCIN B

DESCRIPTION OF THE INVENTION

The present invention relates to a process for preparing known and pharmacologically valuable pyrazomycins, members of the class of C-nucleoside antibiotics. The products obtainable following the instant process are useful as antitumor and antiviral agents.

Following the process of the present invention, one can prepare by synthesis pyrazomycins of the formulas

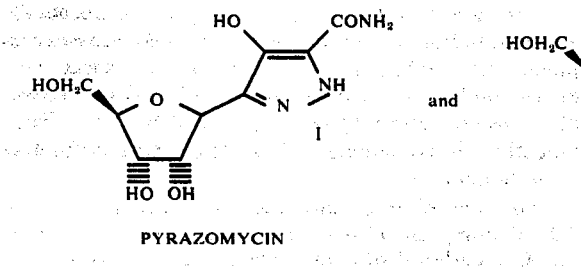

PYRAZOMYCIN

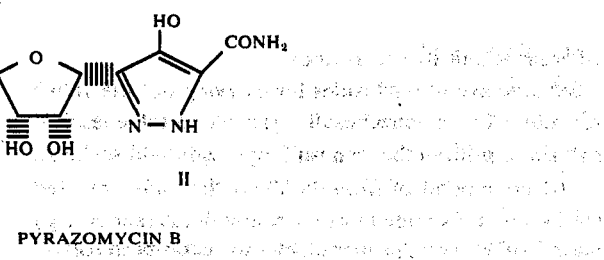

PYRAZOMYCIN B

The compounds of formulas I and II are known compounds, isolated from fermentations of a strain of *Streptomyces candidus* NRRL 3601 as set forth in U.S. Pat. No. 3,802,999 issued Apr. 9, 1974 to Williams et al. which teaching is incorporated herein by reference.

In following the novel process of the present invention the known and useful compounds of formulas I and II above are prepared by the reaction of 2,3-0-isopropylidene-D-ribofuranose i.e., a compound of the formula

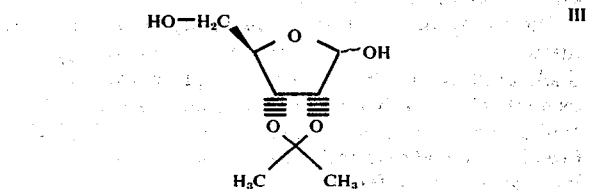

with an aroyl chloride in a solvent such as pyridine or a mixture of pyridine and an inert solvent such as methylene chloride or chloroform to produce a mixture of two anomeric diester derivatives of the formula

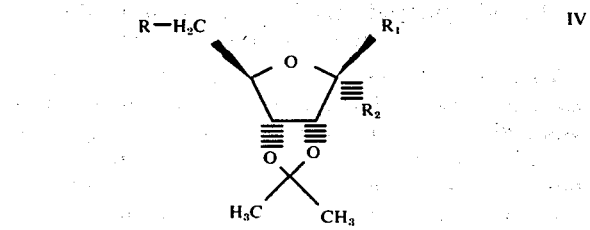

wherein R is an aroyloxy group; $R_1$ is selected from the group consisting of hydrogen and an aroyloxy group and $R_2$ is selected from the group consisting of hydrogen and an aroyloxy group provided however that one of $R_1$ and $R_2$ is hydrogen and the other is aroyloxy.

Typical examples of suitable aroyloxy groups include benzoyl, mono-substituted benzoyloxy groups, such as monohalo or mononitrobenzoyloxy groups and di-substituted benzoyloxy groups, such as dihalo or dinitrobenzoyloxy groups. A particularly preferred substituent group in the above formula IV compound is the p-nitrobenzoyloxy group.

The compounds of formula IV are then reacted with a saturated solution of a hydrogen halide such as hydrogen bromide or hydrogen chloride, preferably hydrogen bromide in an inert solvent such as methylene chloride at a temperature range of $-5°$ to $+25°$ C, preferably at $0°$ C to produce a single ribosyl halide of the formula

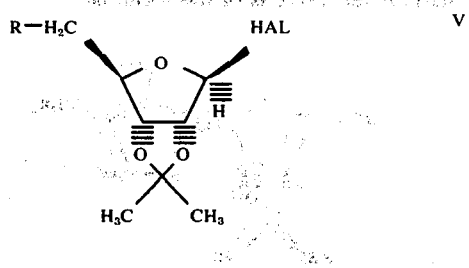

wherein R is an aroyloxy group as above, and HAL is chlorine or bromine.

The compound of formula V is reacted with an alkali metal salt of a di-lower alkyl acetonecarboxylate in an inert compatible solvent such as benzene, toluene, dioxane or dimethoxyethane preferably in the presence of a solid/liquid phase transfer catalyst such as 1,4,7,10,13,16-hexaoxacyclooctadecane which produces the C-alkylation product of the formula

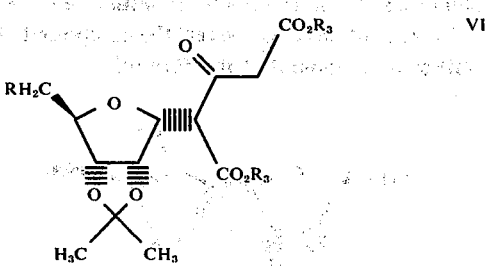

wherein R is as above and $R_3$ is lower alkyl.

The temperature at which the above reaction is carried out is not critical but a temperature range of $0°$ to $50°$ C is preferred with a most preferred temperature being at about room temperature.

The compound of formula VI is then reacted with an alkali metal hydride in an inert solvent such as dimethoxyethane or dioxane to provide the alkali metal salt of the formula VI compound which is subsequently subjected to diazotization with an arylsulfonylazide to produce a compound of the formula

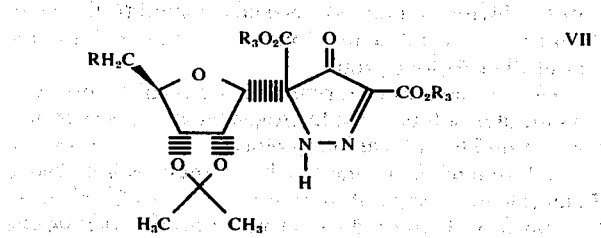

wherein R and R₃ are as above.

Suitable arysulfonylazides for carrying out the above reaction include benzenesulfonyl azide, p-toluenesulfonyl azide, p-bromobenzenesulfonyl azide and so forth.

The compound of formula VII is thereafter reacted with sodium alkoxide in its corresponding alkanol, e.g., methanol, ethanol, propanol, etc. to accomplish solvolysis of the aroyl ester and selective removal of the quaternery alkoxycarbonyl group. The resulting aromatic heterocycle is of the formula

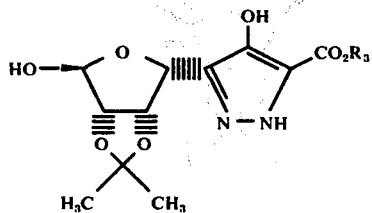

wherein R₃ is lower alkyl.

As above the reaction temperature is not critical but room temperature is most preferred.

The compound of formula VIII is thereafter heated for a period of 2 to 4 hrs., preferably 3 hours at a temperature range of 60° to 120° preferably at 100° C in saturated alcoholic ammonia solution, e.g., methanolic ammonia solution, to convert the compound of formula VIII to a compound of the formula

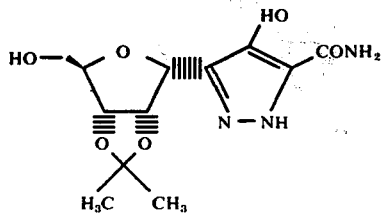

with its epimeric amide obtained as a minor by-product. Prolonged exposure of formula VIII compounds to the above reaction conditions, e.g., approximately 12 hours or more, affords the epimeric amide as the sole product, that is, a compound of the formula

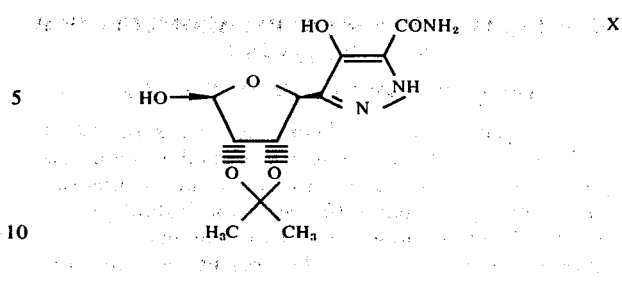

Compounds of formulas IX and X may then be reacted under acidic hydrolysis conditions to remove the isopropylidene protecting group and yield respectively a compound of formula II (Pyrazomycin B) and a compound of formula I (Pyrazomycin). While a wide variety of conditions is available, it is preferred to accomplish this conversion by reacting IX and X with trifluoroacetic acid containing 10% water at about or below room temperature.

As used in this disclosure, the terms "lower alkyl" or "alkyl" comprehend both straight and branched chain ($C_1$–$C_7$) carbon-hydrogen radicals, preferably $C_1$–$C_4$ carbon-hydrogen radicals such as methyl, ethyl, propyl, isopropyl, butyl and the like.

By the term "aroyl" is meant a radical of the formula RCO— wherein R is an aryl group such as phenyl or naphthyl which may be unsubstituted or mono- or di-substituted. Suitable substituents include nitro or halo groups.

The terms "halo" or "halogen" are used to include chlorine, bromine and iodine.

By the term "aryl" is meant an organic radical derived from an aromatic hydrocarbon by the removal of one atom, that is, aromatic moieties such as phenyl, chlorophenyl, tolyl and the like.

The utility of the final products of the above synthetic process are as antiviral and antitumor agents. Such utilities are disclosed in the prior art, see, for example U.S. Pat. No. 3,802,999 issued Apr. 9, 1974 to Williams et al and Sweeney et al.;*Cancer Res.*, 33, 2619 (1973). The above references teachings are herein incorporated by reference.

The compounds of formulas VII and VIII above are novel and as such form part of the present invention.

The following examples are illustrative of the present inventive process. The temperatures referred to are all in the centigrade scale unless otherwise indicated.

EXAMPLE 1

2,3-O-Isopropylidene-1,5-di-O-p-nitrobenzoyl-D-ribofuranoses

To a cold solution of 46.8 g. (0.246 mol) of 2,3-O-isopropylidene-D-ribofuranose in 650 ml. dry pyridine was added in portions, while vigorously stirring, 115 g. (0.62 mol) p-nitrobenzoyl chloride. The reaction mixture was kept stirring for another hour in an ice bath and for 20 hours at room temperature. It was then cooled again and 500 ml. of saturated aqueous NaHCO₃ was carefully added. Upon dilution with 5l. of ice/water a precipiate formed, which was collected by filtration, washed with water and dissolved in 1200 ml. of CH₂Cl₂. The organic solvent was washed with 600 ml. of 0.2 N HCl and with water, dried over Na₂SO₄, and evaporated in vacuo. Crystallization of the residue from CH₂Cl₂-Et₂O afforded 2,3-O-isopropylidene-1,5-di-O-p-nitrobenzoyl-beta-D-ribose, m.p. 139°–140° C.

The mother liquor was evaporated and repeatedly recrystallized from MeOH and CH₂Cl₂-Et₂O. There was obtained pure 2,3-O-isopropylidene-1,5-di-O-p-nitrobenzoyl-alpha-D-ribose having m.p. 157°–158° C.

EXAMPLE 2

2,3-O-Isopropylidene-5-O-p-nitrobenzoyl-beta-D-ribosyl bromide 2,3-O-Isopropylidene-1,5-di-O-p-nitrobenzoyl-beta-D-ribose (8.500 g., 17.4 mmol) was added in one portion to 140 ml. of dry CH₂Cl₂, previously saturated with anhydrous HBr at 0° C. The flask was sealed with a rubber septrum and the reaction was stirred in an ice bath for 30 minutes. It was then allowed to warm to room temperature within one hour. The precipitated p-nitrobenzoic acid was removed by filtration under a blanket of dry argon. The filtrate was concentrated at 25° C. (bath temperature) to approximately one-fourth of the original volume. The solution was repeatedly diluted with dry Et₂O and petroleum ether (b.p. 30°–60° C.) and partially concentrated in vacuo until the bromide crystallized spontaneously on the walls of the flask. After cooling, decanting and washing with petroleum ether, the crystals were dried at room temperature (0.005 mm Hg) affording final product.

An analytical sample was obtained by recrystallization from CH₂Cl₂-Et₂O-petroleum ether; m.p. 118.5°–120.5° C.

The bromide was stable for several days, when stored in a sealed container under argon at −10° C.

EXAMPLE 3

Reaction of 2,3-O-isopropylidene-5-O-p-nitrobenzoyl-beta-D-ribosyl bromide with diethyl 1,3-acetonedicarboxylate To a suspension of 805 mg. (20.07 mmol) KH in 40 ml. of dry benzene (stirred under argon) was added dropwise 4 ml. diethyl 1,3-acetonedicarboxylate, followed by a solution of 3.750 g. (14.2 mmol) "18-crown-6" in 30 ml. of benzene. After H₂-evolution had ceased, a larger excess (22 ml.) of diethyl 1,3-acetonedicarboxylate was added in one portion. Then, a solution of 5.93 g. (14.74 mmolO of 2,3-O-isopropylidene-5-O-p-nitrobenzoyl-beta-ribosyl bromide in 80 ml. of dry benzene was added dropwise over 30 minutes. The reaction mixture was stirred at room temperature for 16 hours (under argon). It was then diluted with 1000 ml. Et₂O. The ether phase was washed with 3 × 300 ml. of H₂O, diluted with 300 ml. of benzene and dried (Na₂SO₄). After evaporation of the solvents under reduced pressure, the excess diethyl 1,3-acetonedicarboxylate was distilled off in a Kugelrohr apparatus (bulb to bulb) at 80°–85° C., 0.01 mm Hg. The residue was dissolved in 15 ml. of toluene/ethyl acetate (10:1) and chromatographed on a column containing 550 g. of a mixture of 75% silica gel G-60 and 25% of silica gel PF-254 (both E. Merck). The column was developed with toluene/ethyl acetate 10:1 (3600 ml. fractions 1–149), 10:1.5 (2300 ml., fractions 15–265), and 10:3 (1300 ml., fractions 266–300). The eluate was monitored by thin layer chromatography in toluene/ethyl acetate 10:1.5 and cyclohexane/ethyl acetate 3:1.

Fractions 80–114, after evaporation and drying in vacuo at 60° C., 0.01 mm Hg, afforded 3-(2,3-O-isopropylidene-5-O-p-nitrobenzoyl-beta-D-ribosyl)oxy-2-pentenedioic acid diethyl ester.

Fractions 115–188, upon evaporation and drying gave 2-(2,3-O-isopropylidene-5-O-p-nitrobenzoyl-alpha-D-ribosyl)-3-oxoglutaric acid diethyl ester. An additional 0.450 g. of the above desired product was obtained upon rechromatographing fractions 189–230, giving a colorless oil.

Fractions 231–310 (combined with the remainder from fractions 189–230) were rechromatographed on 450 g. of silica gel mixture. The column was eluted with ethyl acetate/cyclohexane 25:75 (4200 ml.) and 30:70 (3000 ml.). From appropriate fractions there was obtained after evaporation 3-(2,3-O-isopropylidene-5-O-p-nitrobenzoyl-alpha-D-ribosyl)oxy-2-pentenedioic acid diethyl ester.

Later fractions afforded 2,4-bis(2,3-O-isopropylidene-5-O-p-nitrobenzoyl-alpha-D-robosyl)-3-oxoglutaric acid diethyl ester.

EXAMPLE 4

5-(2,3-O-Isopropylidene-5-O-p-nitrobenzoyl-alpha-D-ribosyl)-4-oxo-2-pyrazoline-3,5-dicarboxylic acid diethyl ester A solution of 4.067 g. (7.77 mmol) of 2-(2,3-O-isopropylidine-5-o-p-nitrobenzoyl-alpha-D-ribosyl)-3-oxoglutaric acid diethyl ester in 80 ml. of dry 1,2-dimethoxyethane (DME) was added during 5 minutes to a stirred suspension of 200 mg. (8.33 mmol) of NaH in 40 ml. of dry DME under argon. An excess of tosyl azide (8 ml.) was then added dropwise with a syringe. After stirring for 3 hours, the reaction was distributed between 1000 ml. of cold ethyl acetate and 500 ml. of ice-water. The aqueous layer was acidified to pH 3 with 1N HCl and extracted with a second portion of ethyl acetate. The extracts were washed with half saturated aqueous NaCl, dried (Na₂SO₄), and evaporated in vacuo.

The residual oil was purified by column chromatography on 500 g. of silica gel. The column was developed with ethyl acetate-cyclohexane 40:60 (4000 ml), then 60:40 (1500 ml.) and finally ethyl acetate (100 ml.). Excess tosyl azide and tosyl amide (m.p. 139, from H₂O) were eluted first. Then fractions were collected, which yielded the final product. Early fractions of this product were almost pure, while later fractions contained small amounts of a new compound, which had formed during the chromatography, and which was identified as the de-ethoxycarbonylation product, 3-(2,3-O-isopropylidene-5-O-p-nitrobenzoyl-alpha-D-ribosyl)-4-hydroxypyrazole-5-carboxylic acid ethyl ester. Analytical samples of the above product were obtained by preparative thin layer chromatography on silica gel with ethyl acetate/cyclohexane, 60:40.

EXAMPLE 5

3-(2,3-O-Isopropylidene-alpha-D-ribofuranosyl)-4-hydroxypyrazole-5-carboxylic acid ethyl ester To a stirred solution of 5.28 g. (9.5 mmol) of 5-(2,3-O-isopropylidene-5-o-p-nitrobenzoyl-alpha-D-ribosyl)-4-oxo-2-pyrazaline-3,5-dicarboxylic acid diethyl ester in 100 ml. abs. EtOH was added 700 mg. of sodium ethoxide. After 45 minutes at 20° C. the reaction was neutralized with AG 50W-X4 ion exchange resin (H⁺, pre-washed with EtOH). The resin was removed by filtration and washed with EtOH. After evaporation of the filtrate in vacuo, the residue was purified by preparative thin layer chromatography on silica gel with ethyl acetate as developing solvent. Elution of the appropriate fractions with ethyl acetate afforded final product.

EXAMPLE 6

3-(2,3-O-Isopropylidene-alpha-D-ribofuranosyl)-4-hydroxypyrazole-5-carboxamide A solution of 600 mg. (1.83 mmol) of the final product of Example 5 in 20 ml. of dry MeOH was saturated with anhydrous $NH_3$ at 20° C. and heated in a sealed tube for 3 hours at 95° C. After evaporation to dryness in vacuo, the residue was chromatographed on 125 g. of silica gel. The column was developed with AcOH—Me$_2$CO—MeOH—H$_2$O, 70:10:5:2.5. Fractions containing the transesterification product and some beta-epimer 3-(2,3-o-isopropylidene-alpha-d-ribofuranosyl)-4-hydroxypyrazole-5-carboxamide were eluted first. These were saved and resubjected to ammonolysis and chromatography as above. Fractions from both reactions containing the desired alpha-epimer and product were combined, evaporated and redissolved in H$_2$O. The aqueous solution was lyophilized to give the final product as a white powder.

EXAMPLE 7

3-(2,3-O-Isopropylidene-beta-D-ribofuranoysl)-4-hydroxypyrazole-5-carboxamide A solution of 600 mg. (1.83 mmol) of the end product of Example 5 in 20 ml. of dry MeOH, was saturated with anhydrous ammonia at 10°–15° C. and heated in a sealed tube for 12 hours at 95°–100° C. After removal of the solvents under reduced pressure, the residue was purified by chromatography on 125 g. of silica gel, with AcOEt-Me$_2$CO-MeOH-H$_2$O, 70:10:5:5 as the solvent. Fractions containing end product were evaporated in vacuo. The residue was redissolved in H$_2$O. The aqueous solution was freeze-dried to afford the end product as a colorless powder.

EXAMPLE 8

3-(alpha-D-Ribofuranosyl)-4-hydroxypyrazole-5-carboxamide

A solution of 335 mg. (1.1 mmol) of the end product of Example 6 in 20 ml. of 90% $CF_3CO_2H$ was kept under argon at room temperature for one hour. Then the solvents were removed at 5° C. under reduced pressure, at last in high vacuum. The residue consisted mainly (>90% by tlc) of the desired pyrazomycin B. It was contaminated with ca. 5% of pyrazomycin which had formed by epimerization during reaction. Purification was accomplished by chromatography on silica gel (125 g.) with EtOAc:Me$_2$CO:MeOH:H$_2$O, 6:1:1:1. Fractions containing the end product were evaporated at low temperature. The residue was redissolved in H$_2$O. The aqueous solution was filtered through a millipore filter and freeze-dried. There were obtained pure Pyrazomycin B as a dihydrate (white powder).

A sample of this end product was recrystallized from H$_2$O. It had mp 76 — Thermal analysis showed a transition from the crystalline form to an amorphous solid at 76° C.

EXAMPLE 9

3-(beta-D-ribofuranosyl)-4-hydroxy-pyrazole-5-carboxamide (pyrazomycin)

A solution of 406 mg. (1.33 mmol) of the end product of Example 7 in 20 ml. of 90% $CF_3CO_2H$ was kept at room temperature for 45 minutes. Then the solvents were removed at 5° C. under reduced pressure, at last in high vacuum. The residue was chromatographed on silica gel with EtOAc:Me$_2$CO:MeOH:H$_2$O, 6:1:1:1. Fractions containing pyrazomycin were evaporated at <20° C. The residue was redissolved in H$_2$O. The aqueous solution was filtered through a millipore filter and lyophylized. Recrystallization from water afforded pyrazomycin, m.p. 112°–115° C., nmp with an authentic sample 112°–115° C.

Both the authentic sample and synthetic material formed higher melting polymorphs, when stored at room temperature. Thermal analysis of freshly recrystallized material showed a broad endothermic phase transistion (melting) at 108° C., partial recrystallization at 117° C. (exotherm) and a second melting range at ca. 170° C. When these samples were heated at 135° C, cooled and reheated, they showed only one phase transistion at 178° C. Thermal analysis of stored samples (3month) revealed one phase transistion (melting point) at 182° C.

What is claimed:

1. A compound of the formula

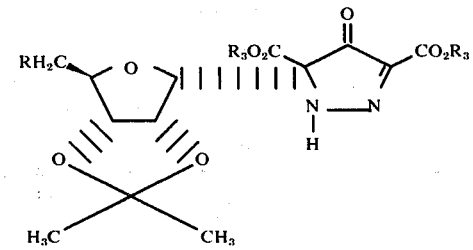

wherein R is selected from the group consisting of benzoyl, monohalo or mono-nitro substituted benzoyloxy groups and di-halo or di-nitro substituted benzoyloxy groups; and $R_3$ is lower alkyl.

2. The compound of claim 1 wherein R is an aroyloxy group selected from the group consisting of benzoyloxy, halo-substituted benzoyloxy, nitro substituted benzoyloxy, dihalo-substituted benzoyloxy and dinitro substituted benzoyloxy.

3. A compound of the formula

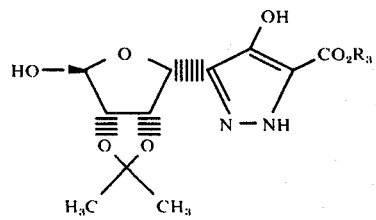

wherein $R_3$ is lower alkyl.

4. A process to produce comounds of the formulas

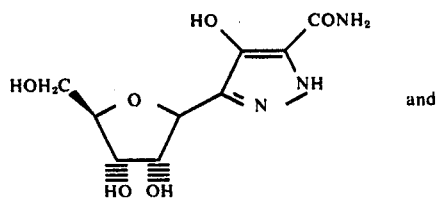 and 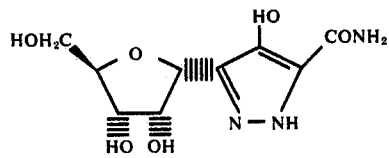

which comprises the steps of:

A. reacting a compound of the formula

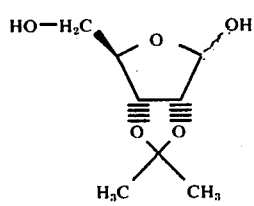

with an aroyl chloride;

B. reacting the product of (A) with a saturated solution of a hydrogen halide;

C. thereafter reacting the product of (B) with the alkali metal salt of a di-lower alkyl acetone carboxylate;

D. reacting the product of (C) with an alkali metal hydride and thereafter subjecting the formed alkali metal salt to diazotization by reacting it with an arylsulfonylazide;

E. reacting the product of (D) with a sodium alkoxide;

F. heating the product at a temperature of from 60° to 120° C of (E) from 2 to 4 hours or for 12 hours or more in a saturated alcoholic ammonia solution;

G. hydrolyzing the products of (F) under acidic conditions to remove the isopropylidene group to form the end products.

* * * * *